(12) United States Patent
Murphy

(10) Patent No.: US 7,022,062 B1
(45) Date of Patent: Apr. 4, 2006

(54) RADIOACTIVE SEED IMPLANTATION SYSTEM AND METHOD

(76) Inventor: Brian B. Murphy, 615 Douglas Ave., Unit D-4, Holland, MI (US) 49423

( * ) Notice: Subject to any disclaimer, the term of this patent is extended or adjusted under 35 U.S.C. 154(b) by 577 days.

(21) Appl. No.: 09/651,603

(22) Filed: Aug. 30, 2000

(51) Int. Cl.
*A61N 5/00* (2006.01)
(52) U.S. Cl. .......................................................... 600/7
(58) Field of Classification Search ................. 600/1–8
See application file for complete search history.

(56) References Cited

U.S. PATENT DOCUMENTS

| | | | |
|---|---|---|---|
| 5,205,289 A * | 4/1993 | Hardy et al. ................... | 600/7 |
| 5,391,139 A * | 2/1995 | Edmundson .................... | 600/7 |
| 5,938,583 A * | 8/1999 | Grimm ........................... | 600/7 |
| 6,206,832 B1 * | 3/2001 | Downey et al. ................ | 600/7 |
| 6,311,084 B1 * | 10/2001 | Cormack et al. .............. | 600/7 |

* cited by examiner

*Primary Examiner*—John P. Lacyk
(74) *Attorney, Agent, or Firm*—William E. Hein

(57) ABSTRACT

A radioactive seed implantation system particularly adapted for use in the treatment of prostate cancer, the system incorporating multiple individually longitudinally and infinitely adjustable needles carrying radioactive seeds which may be simultaneously and precisely implanted in a prostate gland with a minimum of surgical time and operating room expense while minimizing swelling of the gland and reducing patient trauma. An improved method of implanting radioactive seeds in a prostate gland is also disclosed.

21 Claims, 11 Drawing Sheets

RADIOACTIVE SEED IMPLANTATION SYSTEM AND METHOD

BRIEF SUMMARY OF THE INVENTION

This invention relates to radioactive seed implantation systems and, more particularly, to an improved multiple needle radioactive seed implantation system and method particularly adapted for use in the treatment of prostate cancer although it will be understood that the present invention is applicable to other uses.

As is well known, prostate cancer currently affects a significant number of men, particularly those aged 50 years or more. Each year, thousands of men are diagnosed with prostate cancer, and in the past, prostate cancer has often been diagnosed only when it was in an advanced and virtually incurable state. With the introduction of improved diagnostic procedures, including the PSA blood test, and increased public awareness of the situation, prostate cancer is now often being diagnosed at relatively early and curable stages. At the present time there are three fundamental treatments for prostate cancer, including radical surgery, external beam radiation, and radioactive seed implantation. Radical surgery has historically been very effective, but also has a relatively high rate of impotence and incontinence associated with it. External beam radiation has been reasonably effective for treatment of early stages of prostate cancer, and has fewer side effects than radical surgery. After the early stages of the disease, external beam radiation decreases in effectiveness relative to the surgical procedure. The third technique, radioactive seed implantation, involves the placement of radioactive seeds in the prostate gland. The radioactive seeds deliver high dosages of radiation to the prostate, but relatively low dosages to the surrounding tissue, whereby the radiation is closely targeted to the prostate, resulting in the destruction of cancer cells in the gland before they can spread to other parts of the body.

Originally, seed implantation procedures were an open implant technique. In the open technique, the radioactive seeds were placed directly into the prostate gland through a surgical incision. However, this type of implantation has proven to be relatively unsatisfactory since the seeds are difficult to position properly. Recent developments involving radioactive seed implantation are referred to as transperineal seed implantation. This technique, which is described here in greater detail, has had excellent results generally equal to surgery. This technique is advantageous in that it can be preformed on an outpatient basis, permitting the patient to resume normal activities in a few days. The technique has proven to have relatively low incontinence and impotency rates and therefore has become increasingly utilized.

The goal of the transperineal technique is to significantly increase the accuracy of the placement of the radioactive seeds into predetermined locations within the prostate gland. This increase in accuracy is believed to account for the significant success rate of the technique and the other advantages discussed hereinabove. The transperineal technique utilizes a plurality of needles, typically as many as twenty-five to fifty, per treatment to position the seeds within the gland. The needles are inserted one at a time and are used with a specialized stepper apparatus, a transrectal ultrasound probe and a template for positioning and guiding the needles as they are individually moved manually to the desired position within the gland.

The needles used with the transperineal technique have some disadvantages. The insertion of the needles will typically result in movement of the gland. Because the seeds are designed to be placed in precise locations within the gland, this movement of the gland can result in seeds being placed slightly off the desired target area.

The transperineal needles are loaded with the radioactive seeds prior to their insertion in the gland along with spacer elements which separate adjacent seeds. It is, of course, desirable to load the seeds into the prostate gland accurately and quickly. It is also known that in actual practice five or more insertions per needle are typically necessary to position each needle correctly. This may result in significant trauma to the gland, considering that as many as twenty-five to fifty needles are needed for each treatment. Swelling of the gland typically results, which also affects the accuracy of subsequently inserted needles. The accurate and proper placement of the needles is extremely important to the successful use of the seed implantation.

An object of the present invention is to overcome disadvantages in prior radioactive seed implantation systems of the indicated character, and to provide an improved radioactive seed implantation system and method that facilitates exact placement of radioactive seeds in a prostate gland.

Another object of the present invention is to provide an improved radioactive seed implantation system and method that reduces swelling of a prostate gland during implantation of radioactive seeds therein.

Another object of the present invention is to provide an improved radioactive seed implantation system and method which reduces the time required to implant radioactive seeds in a prostate gland and with less trauma to the patient.

Another object of the present invention is that, due to minimized trauma, patients will endure less 'post-surgery' pain which will ultimately lead to a fast and more comfortable recovery.

Another object of the present invention is to reduce operating room time and expense and surgical time and expense required to implant radioactive seeds in a prostate gland.

Another object of the present invention is to provide an improved radioactive seed implantation system and method incorporating multiple, individually longitudinally and infinitely adjustable needles which may be simultaneously implanted in a prostate gland with a minimum of time and expense.

Another object of the present invention is to minimize swelling of a prostate gland due to multiple needles being implanted in a prostate gland.

Another object of the present invention is to provide an improved radioactive seed implantation system that is economical to manufacture and assemble, durable, efficient and reliable in operation.

Another object of the present invention is to greatly minimize the risk of contamination which is considered very high in current procedures.

The above as well as other objects and advantages of the present invention will become apparent from the following description, the appended claims and the accompanying drawings.

DETAILED DESCRIPTION

Figure 1:
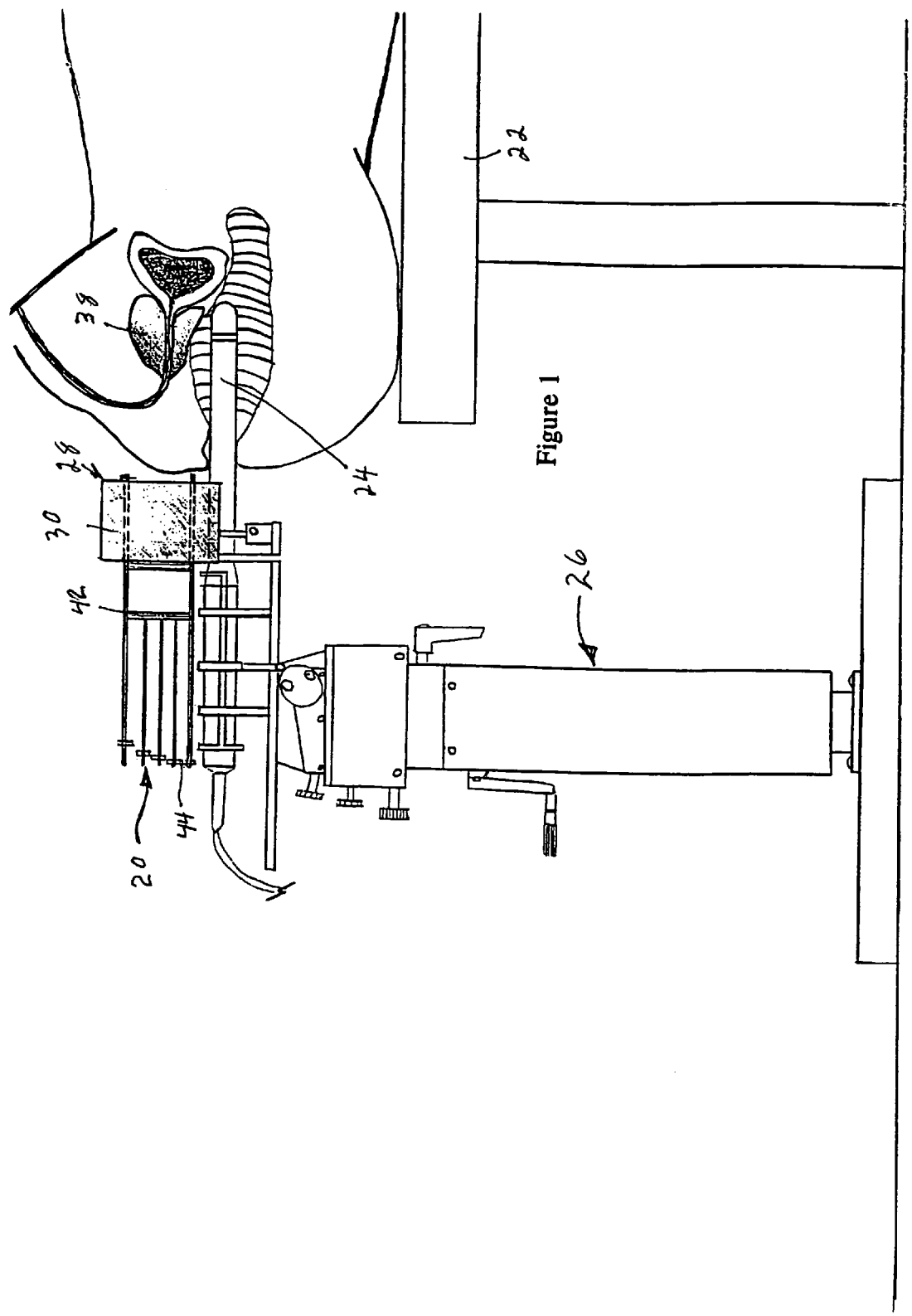
FIG. 1 is a schematic side elevational view of a radioactive seed implantation system embodying the present invention, showing the same installed on a conventional stepping unit in conjunction with a conventional ultrasound probe and a pictorial representation of a patient.
Figure 2:
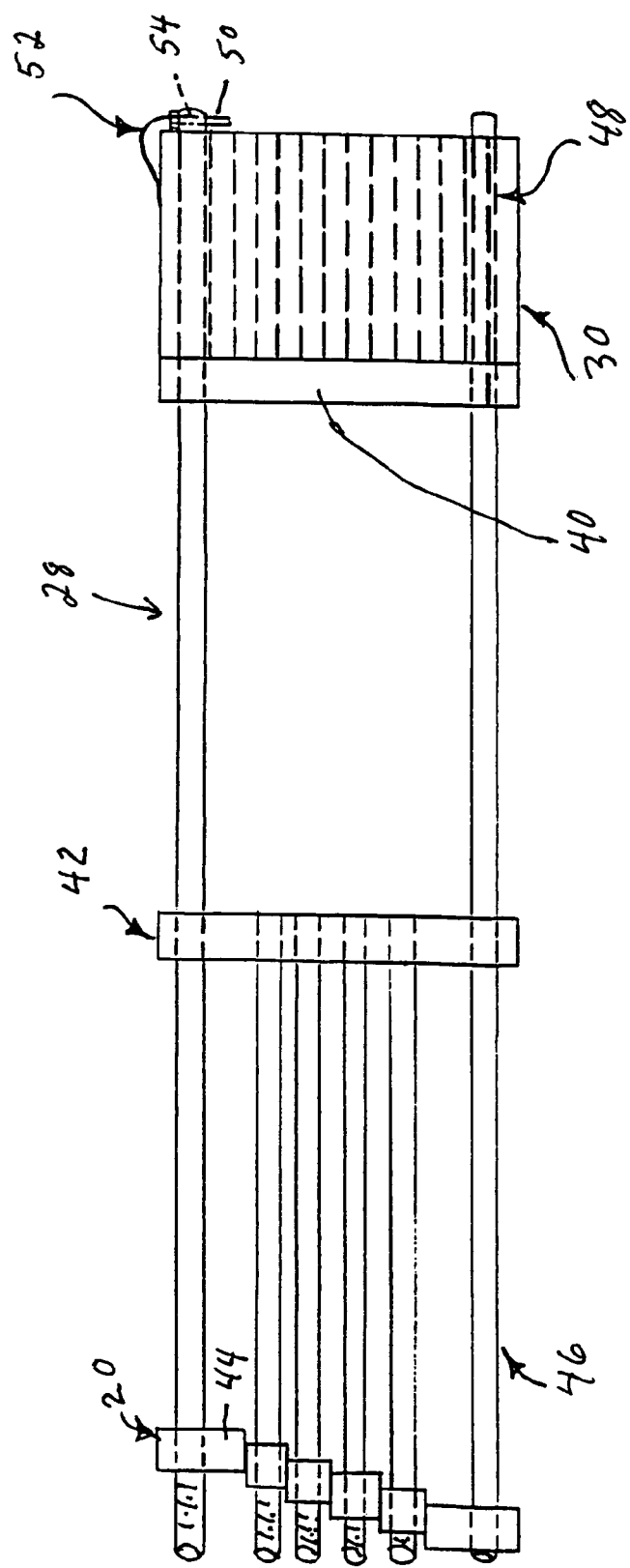
FIG. 2 is a schematic enlarged side elevational view of a portion of the structure illustrated in FIG. 1.
Figure 3:
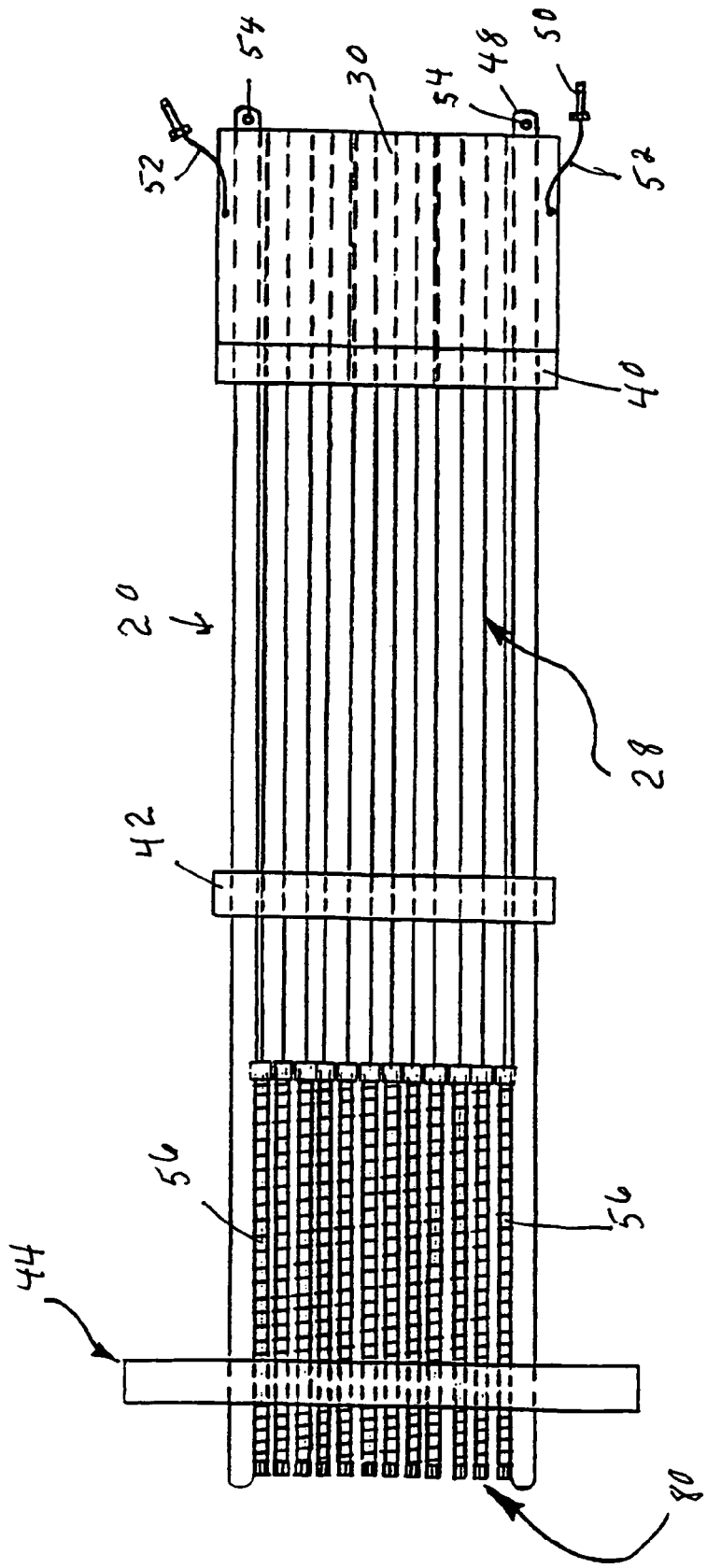
FIG. 3 is a top view of a portion of the structure illustrated in FIG. 2.

Referring to the drawings, the present invention is schematically illustrated therein. In general, in utilizing the radioactive seed implantation system, generally designated 20, embodying the present invention, the patient is placed on an operating table 22, as shown in FIG. 1, and an ultrasonic probe 24 is inserted into the patient's rectum. The ultrasound probe 24 is supported by a conventional stabilizing and stepping unit 26 which may, for example, be of the type marketed by Amertek Medical, Inc. of Singer Island, Fla. under the trademark "SURE-POINT".

Figure 4:
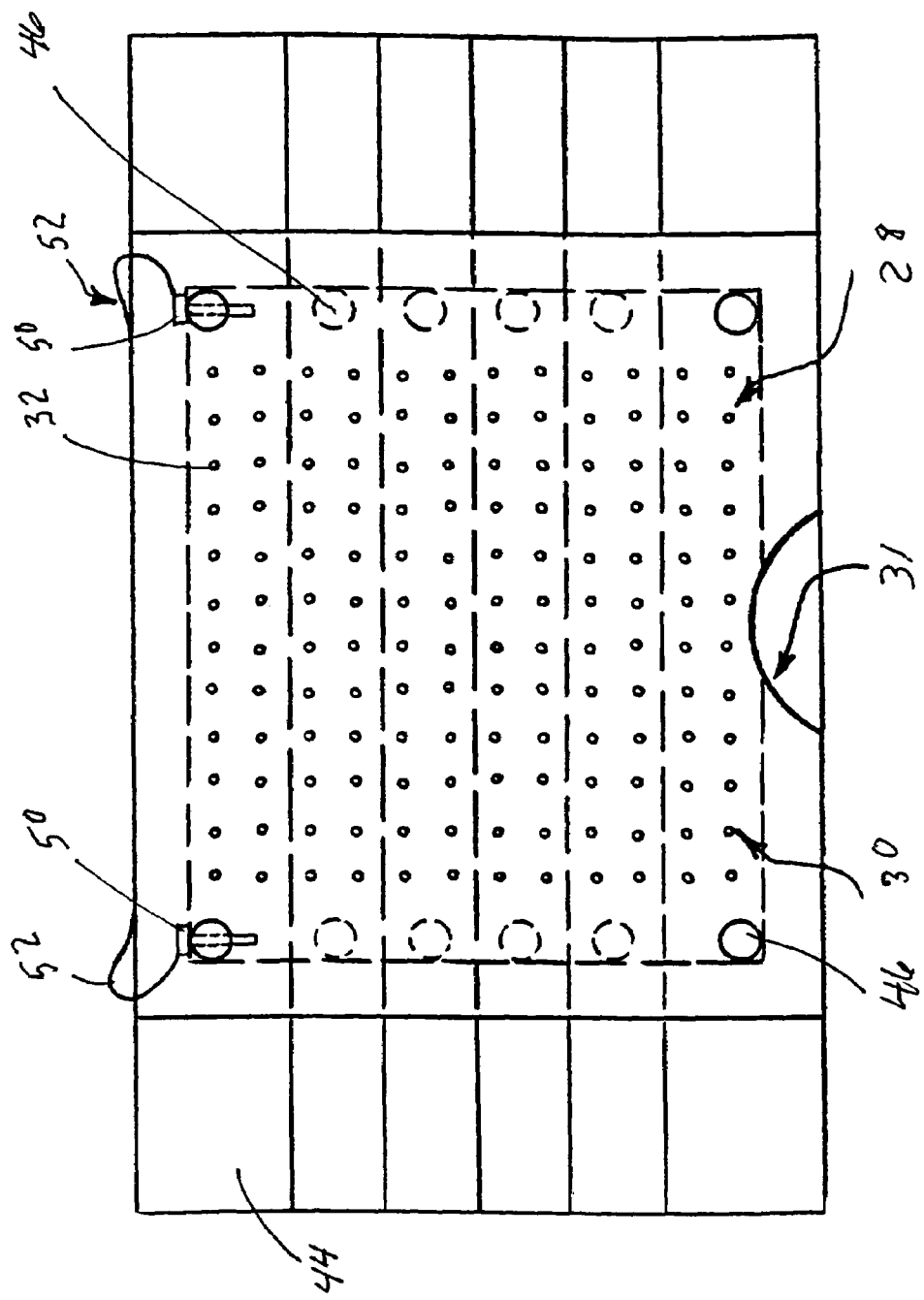
FIG. 4 is a front view of the structure illustrated in FIG. 3.
Figure 5:
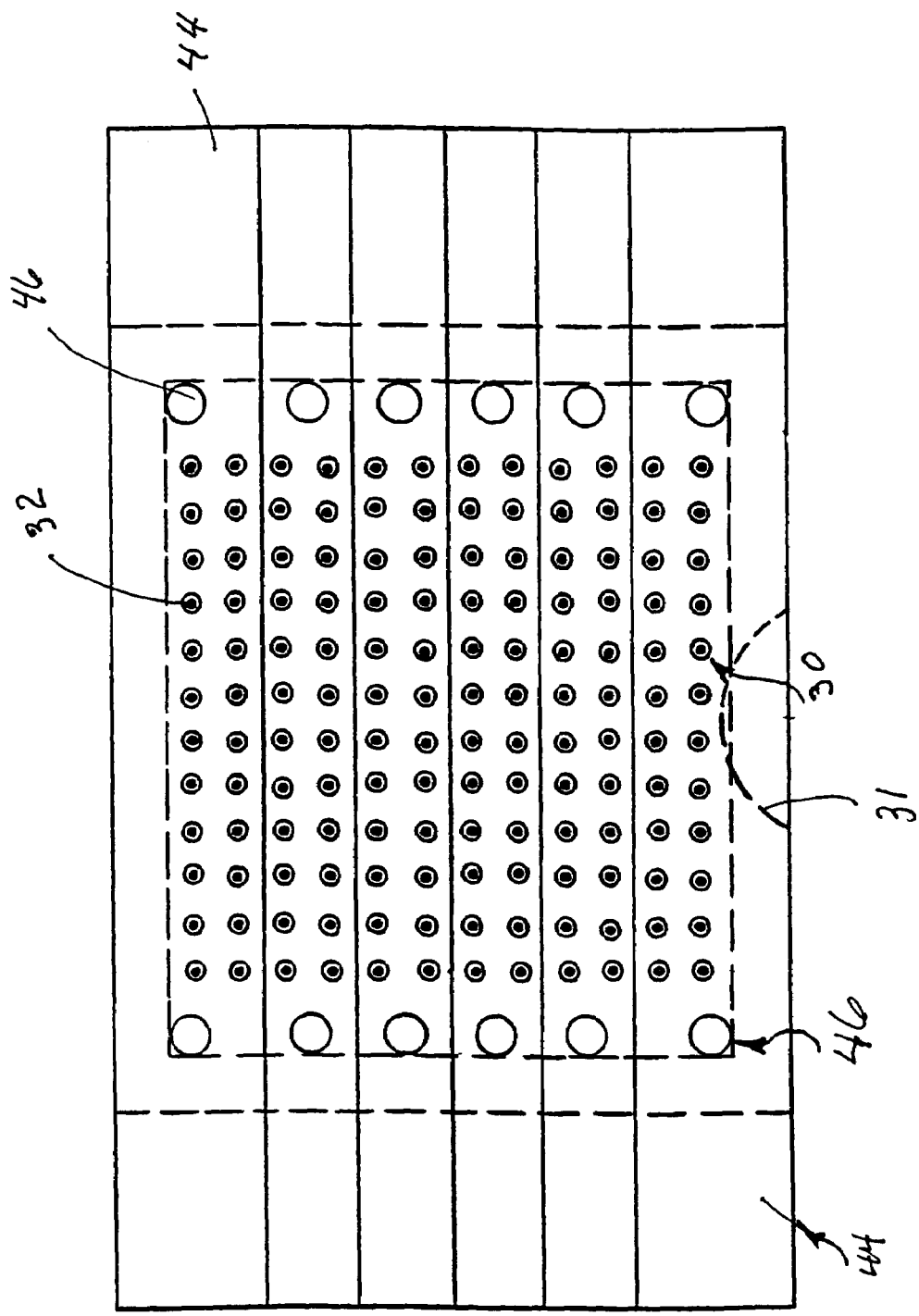
FIG. 5 is a back view of the structure illustrated in FIG. 3.

In accordance with the present invention, a needle support structure, generally designated 28, is provided which is mounted on the stabilizing and stepping unit 26. The support structure is comprised of a guide block 30 which defines a plurality of guide holes 32 arranged in rows and columns and in which individual needles 34 preloaded with radioactive seeds and spacers 36 or 36A are positioned. Any desired or conventional indicia, such as alphabetical letters and/or numerals (not shown) may be applied to the guide block for convenience in identifying the guide holes. In general, a plurality of individually adjustable needles are inserted through the guide block for subsequent implantation in the patient's prostate gland 38. Also, in the embodiment of the invention illustrated, the guide block 30 is provided with a longitudinal arch cutout 31 at the bottom of the block as indicated in FIGS. 4 and 5, the cut-out 31 being adapted to accommodate the top portion of the probe.

As shown in the drawings, the needle support structure 28 also includes a foundation cross bar 40, a stop cross bar 42, and a plurality of push plates 44 mounted on slide bars 46. The guide block 30, which is preferably formed of lead or other radioactive radiation shielding material, is secured to foundation legs 48 through the agency of small push pins 50 connected by wire 52 to the guide block 30 and passing through holes 54 in the adjacent end portions of the foundation legs 48.

In accordance with the present invention, individually adjustable screws 56 are precisely machine threaded into the push plates 44, an adjustable depth screw 56 being provided for each needle 34 in the grid of rows and columns of guide holes 32 whereby the depth of penetration of each needle 34 into the prostate gland 38 may be individually longitudinally and infinitely adjusted within the operating range of the system 20. In the embodiment of the invention illustrated, 144 needles 34 may be accommodated in the needle supporting structure 28, it being understood that the needle supporting structure may be designed to accommodate any desired number of needles. Also in the embodiment of the invention illustrated, six push plates 44 are provided with each push plate 44 accommodating two rows of needles 34, it being understood that movement of the push plates 44 toward the guide block 30 is stopped by the cross bar 42. It will also be understood that any desired number of rows of needles 34 may be provided which may be accommodated by any desired number of individual push plates 44, as for example one row of needles per push plate or as many as six rows of needles may be accommodated by one push plate in the embodiment of the invention illustrated. Again, any desired or conventional indicia, such as combinations of alphabetical letters and/or numerals (not shown) may be applied to the push plates to identify the rows and columns of needles associated with the push plates.

Figure 6:
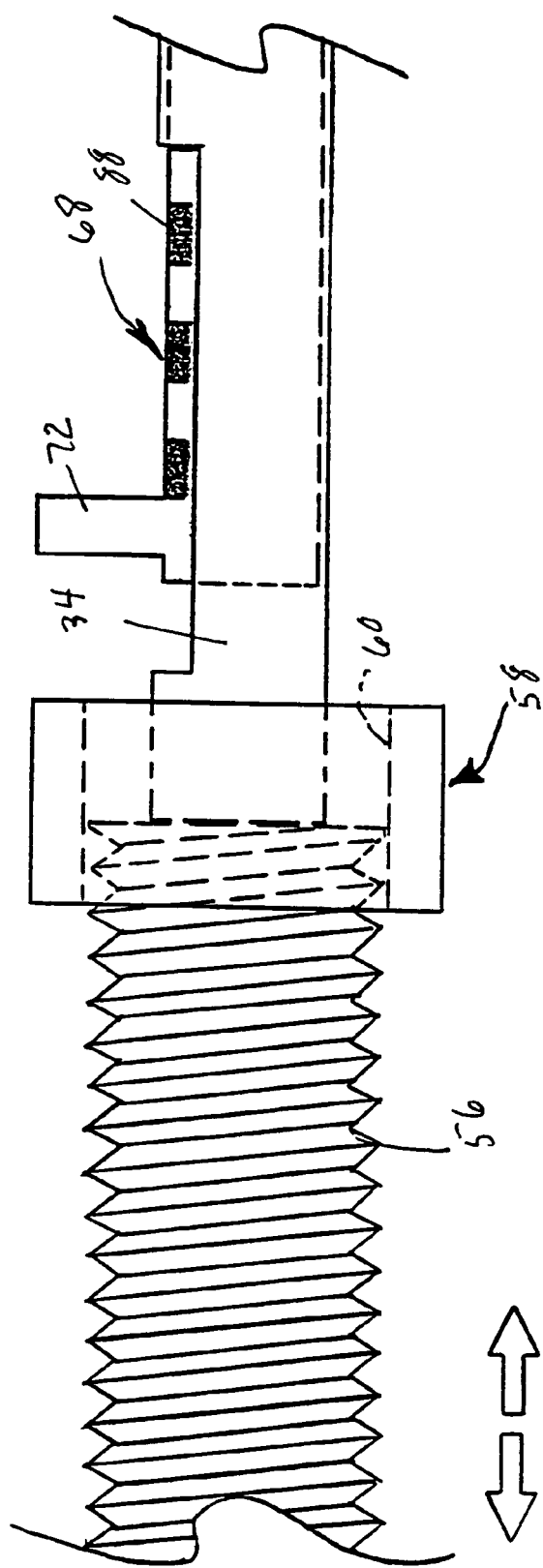
FIG. 6 is an enlarged view of the adjustable screw and needle connection illustrated in FIG. 3.

FIG. 6 illustrates the manner in which each of the screws 56 is connected to the implant needle 34 associated therewith, which needles will be described hereinafter in greater detail. As shown in FIG. 6, a cap 58 is provided on the end of each screw 56, the cap 58 defining a recess 60 adapted to receive the adjacent end portion of an associated needle with a loose fit. With such a construction, the screws 56 may be easily disconnected from the associated needles after the needles have been pushed to a predetermined depth in the prostate gland 38 being treated. Each needle 34 will thus remain in the predetermined position within the gland until the needle is pulled back manually as will be described hereinafter in greater detail.

Figure 11:
FIG. 11 is an enlarged schematic elevational view of needle structure embodying the present invention.
Figure 12:
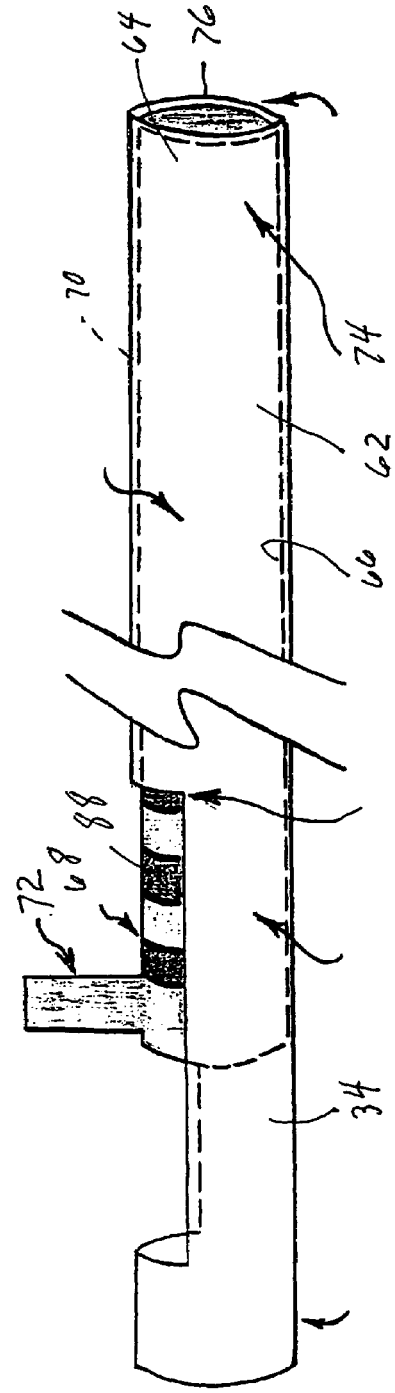
FIG. 12 is an enlarged schematic view, with portions broken away, of the needle structure illustrated in FIG. 11.
Figure 13:
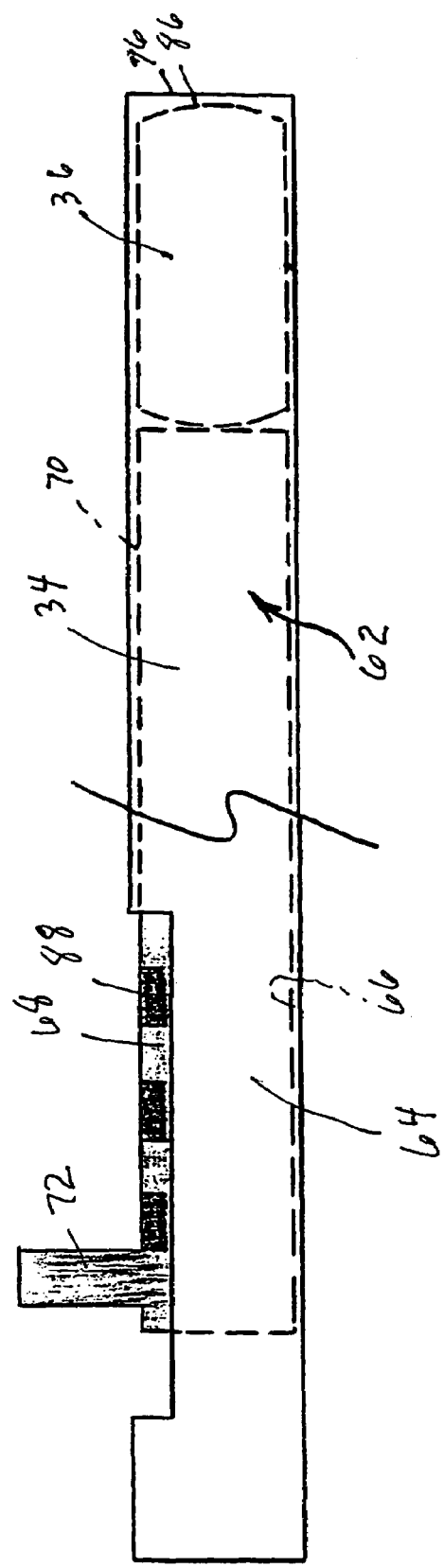
FIG. 13 is a schematic elevational view, with portions broken away, illustrating the manner in which radioactive seeds or spacers are preloaded into needles embodying the present invention.

As shown in FIGS. 6, 11 and 12, each needle 34 is comprised of an elongate tube 62 which is formed of rigid material, such as surgical stainless steel, the wall 64 of the tube defining an internal passageway 66 adapted to receive an elongate push rod 68 with a sliding fit. The wall 64 of the tube also defines an elongate slot 70 adapted to receive a push tab 72 provided on the push rod 68 and projecting radially outwardly therefrom. With such a construction, preloaded spacers and radioactive seeds, sheathed by the associated needle as illustrated in FIGS. 11 and 13, may be unsheathed from the needle by manually holding the push tab 72 in a fixed position while simultaneously withdrawing the needle longitudinally relative to the push rod. If desired, the push rod 68 may be held in place through the agency of a needle-nosed instrument such as surgical needle-nosed pliers (not shown), and/or the needle may be withdrawn simultaneously using the same or a similar instrument.

As shown in FIGS. 11 and 12, the end 74 of the tubular needle remote from the screw connecting end thereof is preferably provided with a razor sharp edge 76. Such a construction, along with the needle being formed of rigid material, minimizes deflection of each needle as it is inserted into the gland through the agency of the push plates.

Figure 7:
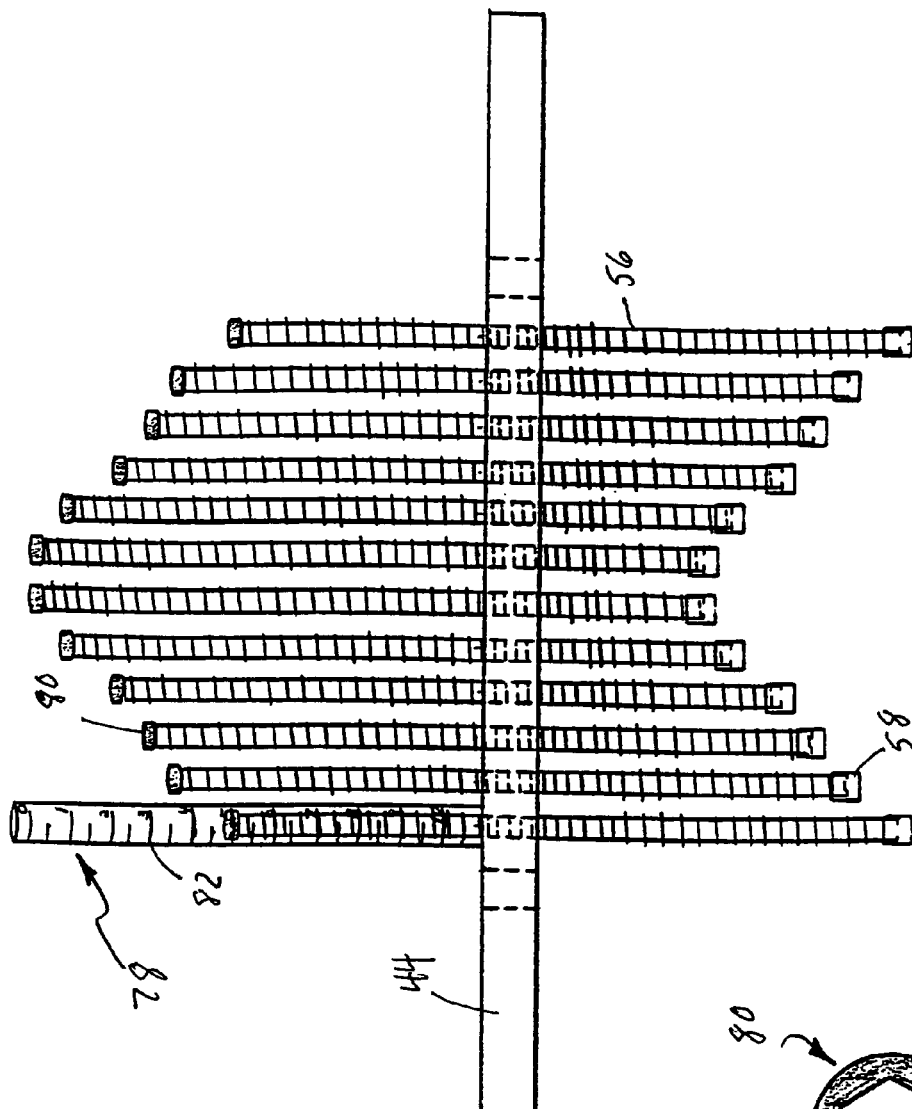
FIG. 7 is an enlarged top view of a portion of the structure illustrated in FIG. 3 and illustrating the manner in which a measurement tube may be applied to the adjustment screws incorporated in the system embodying the invention.
Figure 8:
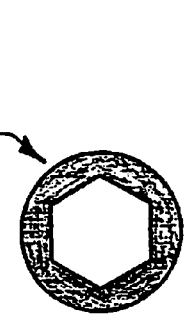
FIG. 8 is an enlarged end view of a wrench fitting provided on the end of each adjustment screw.
Figure 9:
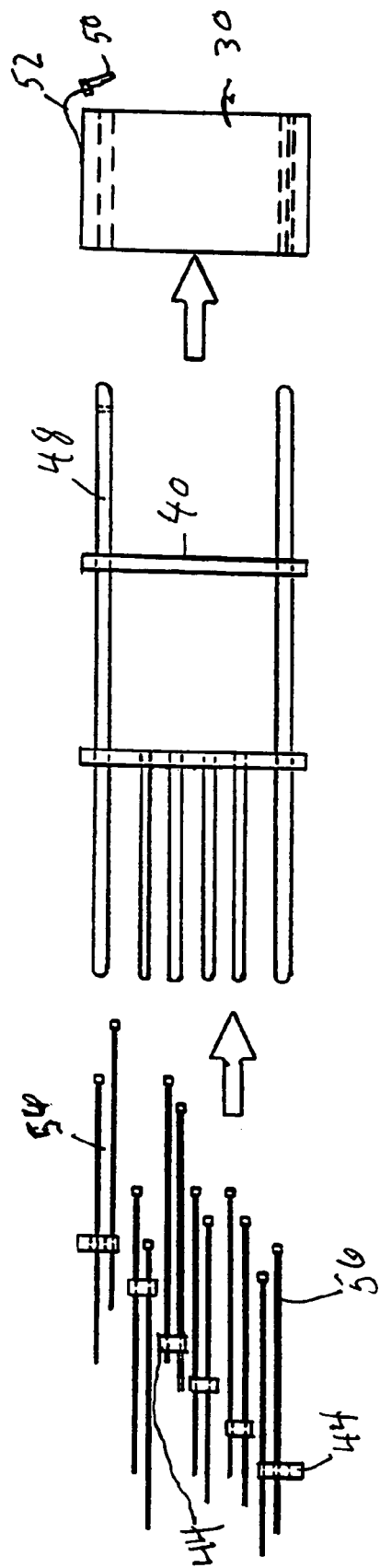
FIG. 9 is a schematic exploded view of a portion of the structure illustrated in FIG. 3.
Figure 10:
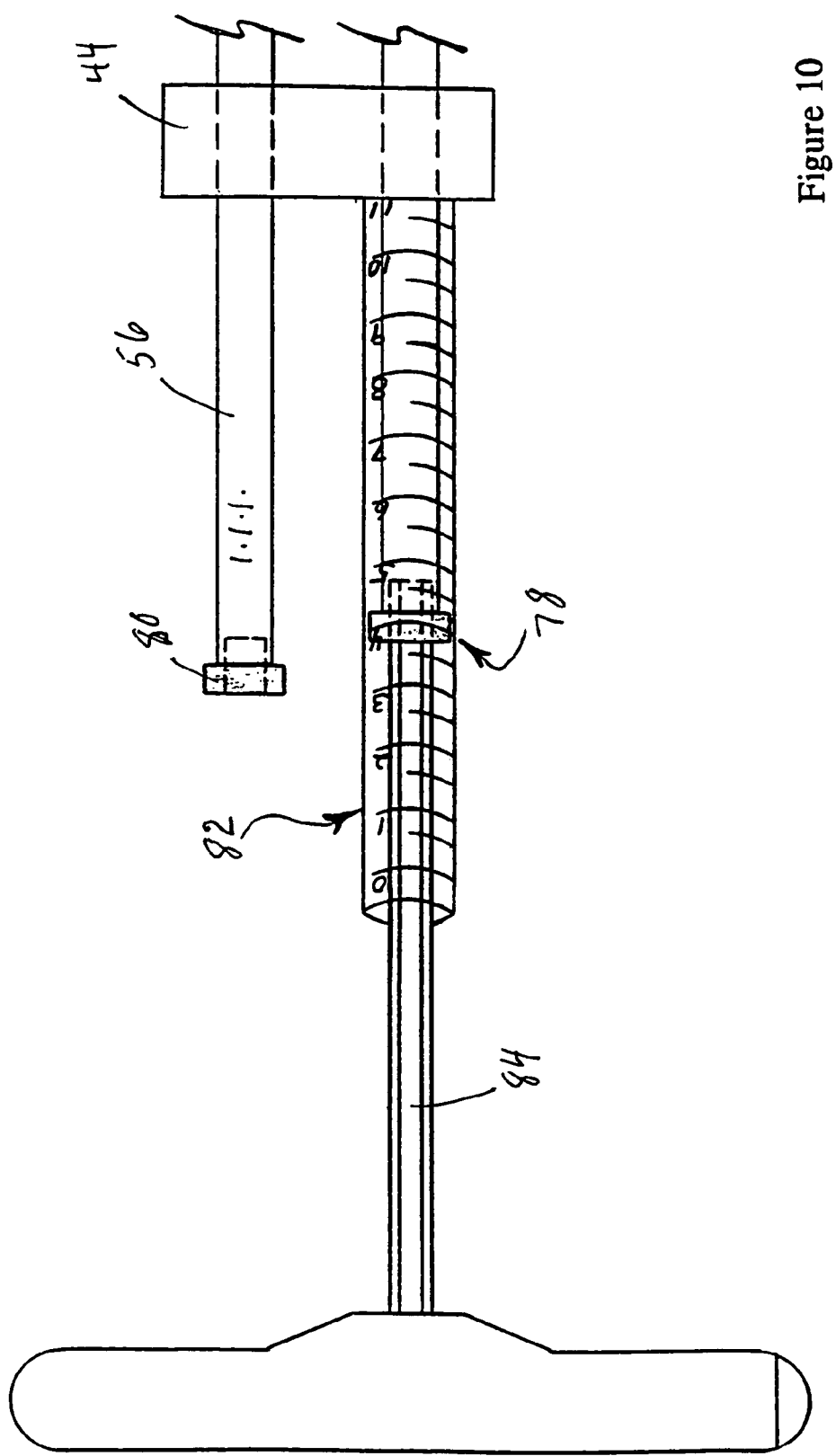
FIG. 10 is an enlarged schematic view of a portion of the structure illustrated in FIG. 7 and illustrating the manner in which the needles are adjusted longitudinally.

In utilizing the radioactive seed implantation system 20 embodying the present invention, the prostate gland 38 of the patient is initially mapped utilizing the ultrasound probe 24 and the stepper apparatus 26 to establish a preplanned radiation therapy seed pattern. Such preplanned radiation pattern effected by the mapping of the gland is then utilized to position each needle 34 in a desired longitudinal position through the agency of the screws 56 previously described whereby the radiation seeds will be deposited in the desired locations in the gland. In that connection, a clear measurement tube 78 which fits over each screw as shown in FIG. 7 may be utilized to set each needle 34 to a predetermined position whereby each needle will be inserted into the gland to a predetermined precise depth. The Allen-wrench fitting 80 provided on the end of each screw as illustrated in FIGS. 7 and 8 facilitates rotation of each screw in the associated pusher plate. The gradations 82 on the measurement tube 78 may be utilized in conjunction with the end surface of the screw to position each needle to the desired location.

If desired, the mapping of the patient's prostate gland may take place as much as several weeks prior to scheduled surgical insertion of the seeds in the gland, thereby allowing sufficient time to position each of the needles in the support structure in the desired predetermined location. The screws 56 are adjusted on one push plate at a time prior to sliding the plates on the slide bars 46, and the clear measurement tube 78 also acts to guide in the Allen-wrench 84 thereby reducing setup time. As previously mentioned, the needle support structure may comprise one or more push plates, as desired. For example, one push plate may be adapted to accommodate all of the needles or multiple push plates may be provided, each adapted to accommodate some of the needles.

During the surgical implantation procedures, the ultrasound probe 24 is utilized to verify that the needles 34 are inserted to the previously determined desired longitudinal positions and that the radioactive seeds and spacers are deposited in the gland 38 at the previously determined desired locations. In that connection, the end space 86 in each needle may, for example, be filled with "bone wax" or other conventional material, to contain the seeds and spacers until the push rod 68 is activated. If desired, in utilizing the radioactive seed implantation system 20 embodying the present invention, increment markings 88 may be provided on the push rods, as illustrated in FIGS. 6, 12 and 13, for ease in verifying the position of the push rod within the associated hollow needle. It should be understood that the tabs are all individually preset when the needles are pre-loaded.

In utilizing the radioactive seed implantation system 20 embodying the present invention, each needle 34 is pre-loaded with a predetermined number of radioactive seeds 36 for the particular location where each needle is to be inserted into the prostate gland. The seeds in the needle are usually separated by spacers, as illustrated in FIGS. 11 and 13, so that the seeds and spacers alternate within a portion of the hollow needle, the spacers being conventional spacers made of material which can be accommodated in living human tissue and of the type utilized in prior single needle insertion techniques. An internal sliding push rod 68 is also positioned within the associated needle with the end of the push rod remote from the tab 72 abutting the adjacent seed 36 disposed in the needle. After the needle has been inserted in the prostate gland, the associated screw 56 may be disconnected from the needle, and the needle may be manually withdrawn from the prostate gland while the push rod 68 is held in place through the agency of the radially projecting tab 72. As each needle is withdrawn, the line of successive seeds and spacers within each needle is unsheathed from the needle, and the seeds and spacers remain in the gland. Thus the rod 68 and the seeds and spacers never really move as the needle cylinder is retracted backwardly in an unsheathing action with the result that the seeds and spacers are implanted at the desired positions within the gland. Of course, the rod is subsequently removed from the gland. It will be understood that after all of the seeds and spacers have been deposited in the gland, as for example the seeds and spacers in thirty to fifty needles, and the ultrasound probe 24 has verified that the seeds and spacers have been deposited in the predetermined desired locations, the ultrasound probe 24 may be withdrawn from the patient. The radioactive seeds may be formed of Iodine 125, Palladium 103 or other suitable radioactive material as desired.

The insertion of multiple needles in the gland through the agency of the push plates causes much less trauma to the patient as compared with the prior technique of inserting needles one at a time into the gland, and there is much less swelling of the gland because there is only one cut per coordinate, and because the time required to insert all of the needles is materially reduced, as for example it may take 2 and ½ hours to insert all of the needles one at a time, whereas the present invention enables all of the needles to be inserted in about 20 minutes or less.

While a preferred embodiment of the invention has been illustrated and described, it will be understood that various changes and modifications may be made without departing from the spirit of the invention.

What is claimed is:

1. A seed implantation system comprising, in combination, a support structure, a plurality of spaced hollow needles carried by said support structures, seeds disposed in said plurality of spaced hollow needles and sheathed thereby, means for individually adjusting the longitudinal positions of said needles relative to each other, means for simultaneously inserting said plurality of spaced hollow needles in predetermined positions in a patient whereby the sheathed seeds and the needles are disposed in predetermined positions within the patient, and means for unsheathing said seeds from such needles at said predetermined positions within the patient.

2. The combination as set forth in claim 1, each needle having a tubular wall defining an elongate slot extending longitudinally of said needle, said means for unsheathing said seeds including a tab disposed in said slot and projecting radially outwardly of said needle thereby enabling relative movement of said needle relative to said seeds.

3. The combination as set forth in claim 1, a leading end of each of said needles being of sharp tubular configuration.

4. The combination as set forth in claim 1, said means for adjusting the longitudinal positions of said needles relative to each other including screw means rotatable relative to said needles.

5. The combination as set forth in claim 4 including means releasably connecting said needles to said screw means.

6. The combination as set forth in claim 1, said support structure including a guide block defining a plurality of passageways each adapted to receive and support an individual needle for longitudinal movement relative to said support structure.

7. A radioactive seed implantation system for use in treatment of prostate cancer, said system comprising, in combination, a support structure, a guide block fixed to said support structure and defining a plurality of guide passageways disposed in rows and columns and adapted to receive elongate needles, a stop member fixed to said support structure and disposed in spaced relationship with respect to said guide block, a push plate mounted on said support structure for relative movement with respect to said stop member, a plurality of elongate needles releaseably connected to said push plate for simultaneous longitudinal movement with respect to said guide block, said needles being of tubular configuration and defining an elongate passageway therein, radioactive seeds received and sheathed within said elongate passageway of said needles, and means for unsheathing said seeds from said needles in predetermined locations in the prostate gland of a patient.

8. The combination as set forth in claim 7, each of said needles having a tubular wall defining an elongate slot, said means for unsheathing said seeds from said needles including an elongate push rod having a tab projecting radially outwardly through said elongate slot defined by the tubular wall of the associated needle.

9. The combination as set forth in claim 7, and screw means for individually adjusting the longitudinal positions of said needles relative to the associated push plate.

10. The combination as set forth in claim 9, the portion of each needle remote from the associated push plate having a sharp tubular end disposed at right angles with respect to the longitudinal axis of the needle.

11. The combination as set forth in claim 9, and means for measuring the longitudinal positions of said needles relative to the associated push plate.

12. The combination as set forth in claim 9, and wrench means for effecting rotation of said screw means relative to the associated push plate.

13. A radioactive seed implantation system for use in treatment of prostate cancer, said system comprising, in combination, a support structure, a guide block fixed to said support structure and defining a plurality of guide passageways disposed in rows and columns and adapted to receive elongate needles, a stop member fixed to said support structure and disposed in spaced relationship with respect to said guide block, a push plate mounted on said support structure for relative movement so as to engage said stop member, a plurality of elongate needles releaseably connected to said push plate for simultaneous longitudinal movement with respect to said guide block, said needles being of tubular configuration and defining an elongate passageway therein, radioactive seeds received and sheathed within said elongate passageway of said needles, and means for unsheathing said seeds from said needles at predetermined locations in the prostate gland of a patient.

14. The combination as set forth in claim 13, each of said needles having a tubular wall defining an elongate slot, said means for unsheathing said seeds from said needles including an elongate push rod having a tab projecting radially outwardly through said elongate slot defined by the tubular wall of the associated needle.

15. The combination as set forth in claim 14, and screw means for individually adjusting the longitudinal positions of said needles relative to the associated push plate.

16. The combination as set forth in claim 15, the portion of each needle remote from the associated push plate having a sharp tubular end disposed at right angles with respect to the longitudinal axis of the needle.

17. The combination as set forth in claim 16, and measuring means for setting the longitudinally adjusted positions of said needles relative to each other.

18. The combination as set forth in claim 15 including wrench means for effecting rotation of said screw means relative to the associated push plate.

19. An implant needle structure comprising: an implant needle of tubular configuration and having a tubular wall defining an elongate passageway, said tubular wall defining an elongate slot communicating with said passageway; and an elongate push rod disposed in said passageway of said implant needle and having a tab portion projecting radially outwardly through said slot.

20. The combination as set forth in claim 19, one end portion of said wall having a sharp tubular end disposed at right angles with respect to the longitudinal axis of said passageway.

21. A method of implanting radioactive seeds in a prostate gland of a patient comprsing the steps of establishing a preplanned radiation seed pattern; preloading a plurality of needles with radioactive seeds located in predetermined positions therein; individually longitudinally and infinitely adjusting said needles relative to each other whereby the seeds are disposed in said predetermined seed pattern; simulatneously inserting a plurality of said needles into the prostate gland of a patient to a predetermined depth; and thereafter withdrawing the needles from the gland while maintaining the seeds in their predetermined seed pattern within the gland.

* * * * *